United States Patent
Schulat et al.

(10) Patent No.: US 7,808,645 B2
(45) Date of Patent: Oct. 5, 2010

(54) ANALYSIS SYSTEM FOR ANALYZING A SAMPLE ON AN ANALYTICAL TEST ELEMENT

(75) Inventors: Jochen Schulat, Mannheim (DE); Klaus-Dieter Steeg, Kronau (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/963,801

(22) Filed: Dec. 22, 2007

(65) Prior Publication Data

US 2008/0144022 A1    Jun. 19, 2008

Related U.S. Application Data

(63) Continuation of application No. PCT/EP2006/063145, filed on Jun. 13, 2006.

(30) Foreign Application Priority Data

Jun. 22, 2005    (EP) ................................ 05 013 452

(51) Int. Cl.
    *G01N 21/47* (2006.01)
(52) U.S. Cl. ................ 356/446; 356/39; 422/82.05
(58) Field of Classification Search ......... 356/432–440, 356/39, 402, 427; 422/50, 99–103, 82.05, 422/82.09
    See application file for complete search history.

(56) References Cited

U.S. PATENT DOCUMENTS

| | | | |
|---|---|---|---|
| 4,141,649 A | | 2/1979 | Schnall et al. |
| 5,424,035 A | | 6/1995 | Hones et al. |
| 5,706,140 A | | 1/1998 | Nishino et al. |
| 5,846,837 A | | 12/1998 | Thym et al. |
| 5,995,236 A | * | 11/1999 | Roth et al. ................ 356/445 |
| 6,036,919 A | * | 3/2000 | Thym et al. ................ 422/58 |
| 6,055,060 A | * | 4/2000 | Bolduan et al. ............ 356/433 |
| 6,560,040 B2 | * | 5/2003 | Kaneko et al. ............. 359/739 |
| 6,574,425 B1 | * | 6/2003 | Weiss et al. ................ 356/402 |
| 6,707,554 B1 | | 3/2004 | Miltner et al. |
| 7,262,061 B2 | | 8/2007 | Petrich et al. |
| 2003/0102483 A1 | * | 6/2003 | Yamamoto et al. .......... 257/99 |
| 2004/0007244 A1 | | 1/2004 | Harms |
| 2004/0112920 A1 | * | 6/2004 | Felten et al. ................ 222/212 |

(Continued)

FOREIGN PATENT DOCUMENTS

CA    2311496    6/1999

(Continued)

OTHER PUBLICATIONS

Roche Diagnostics GmbH product description of Accu-Check Compact blood sugar measuring system, www.accu-chek.de, Jan. 19, 2006.

*Primary Examiner*—Hoa Q Pham
(74) *Attorney, Agent, or Firm*—Bose McKinney & Evans LLP

(57) ABSTRACT

The invention relates to an analysis system for analysing a sample on an analytical test element. The analysis system comprises a measuring module for carrying out measurements on the sample on the analytical test element and an optical module which comprises a lens and a diaphragm by which the light can be focused. The lens and the diaphragm of the optical module are combined as one piece in a multi-component injection-molded part.

14 Claims, 6 Drawing Sheets

U.S. PATENT DOCUMENTS

| | | |
|---|---|---|
| 2004/0120053 A1 | 6/2004 | Hendriks |
| 2006/0113276 A1* | 6/2006 | Rohrig ........................ 215/388 |
| 2007/0030334 A1* | 2/2007 | Nishizawa .................. 347/245 |
| 2008/0053201 A1* | 3/2008 | Roesicke et al. ........... 73/61.41 |

FOREIGN PATENT DOCUMENTS

| | | |
|---|---|---|
| DE | 26 37 514 | 2/1978 |
| DE | 44 31 744 | 4/1995 |
| DE | 197 53 847 | 6/1999 |
| DE | 198 44 500 | 3/2000 |
| DE | 10220671 A1 * | 12/2003 |
| DE | 102 61 974 | 2/2004 |
| EP | 0 618 443 | 10/1994 |
| EP | 0 821 233 | 1/1998 |
| EP | 0 821 234 | 1/1998 |
| WO | WO 93/02720 | 2/1993 |
| WO | WO 97/02487 | 1/1997 |
| WO | WO 00/19185 | 4/2000 |
| WO | WO 01/48461 | 7/2001 |

* cited by examiner

ANALYSIS SYSTEM FOR ANALYZING A SAMPLE ON AN ANALYTICAL TEST ELEMENT

RELATED APPLICATIONS

This application is a continuation application of International Application PCT/EP2006/063145, filed Jun. 13, 2006, which claims priority to EP 05 013 452.7, filed Jun. 22, 2005, which are hereby incorporated by reference in their entirety.

BACKGROUND

The present invention relates to an analysis system for analyzing a sample on an analytical test element with an optical module.

For the analysis of samples, for example, body fluids such as blood or urine, use is often made of analysis systems in which the samples to be analyzed are located on a test element and react in a test area with one or more reagents on the test element before they are analyzed. Optical, in particular, photometric, as well as electrochemical evaluation of test elements are the most commonly used methods for rapidly determining the concentration of analytes in samples. Analysis systems with test elements for sample analysis are generally used in the field of analytics, environmental analytics, and in particular, in the field of medical diagnostics. In the field of blood glucose diagnostics using capillary blood, test elements which are photometrically or electrochemically evaluated are of great value.

There are various forms of test elements. Essentially square, small plates, also referred to as slides, in the middle of which there is a multilayered test area, are known, for example. Diagnostic test elements of a strip-shaped form are commonly referred to as "test strips." Test elements are extensively described in the prior art, for example, in the documents DE 19 753 847, EP 0 821 233, EP 0 831 234 or WO 97/02487. The present invention relates to test elements of any form, in particular, to test elements in the form of strips.

For the analytical examination of a sample on a test element, the prior art discloses test element analysis systems which contain a test element holder for positioning the test element in a measuring position and a measuring and evaluation device for carrying out a measurement and determining an analysis result.

WO 00/19185 A1 relates to a device for the photometric evaluation of test elements, comprising an illuminating unit with at least a first and a second light source, a holder for receiving a test element with a detection zone in such a way that the detection zone is positioned with respect to the illuminating unit, a detection unit with at least one detector, which detects light reflected by the detection zone or transmitted through the detection zone, a control unit, which activates the two light sources and records the signal generated by the detection unit as a detection signal, and an evaluation unit, which evaluates the detection signals in order to determine the analyte concentration contained in the sample.

EP 0 618 443 A1 relates to a test strip analysis system comprising an evaluation device with a test strip holder and suitable test strips. The strip holder serves the purpose of positioning the test strip in a defined position with respect to a measuring unit. It has a test strip support and a guide for the test strip.

WO 01/48461 A1 concerns a test element analysis system for the analytical examination of a sample. The analysis system comprises test elements with a supporting film and a test area which is attached to a flat side of the supporting film and, to carry out the analysis, is brought into contact with the sample in such a way that liquid sample constituents penetrate into the test area. The test area contains a reagent system which, when it reacts with constituents of the sample, leads to an optically measurable change in a detection zone that is characteristic of the analysis and which occurs on the side of the test area facing the supporting film. Furthermore, the analysis system comprises an evaluation device with a test element holder for positioning a test element in a measuring position and a measuring device for measuring the optically measurable change in the detection zone, the measuring device having a light transmitter for illuminating the detection zone with primary light and a detector for detecting the secondary light thereby diffusely reflected by the detection zone.

Many such known analysis systems have at least one optical module, which may comprise, inter alia, a lens and a diaphragm, by which the light can be focused. These optical modules are produced in the prior art from a number of individual parts, which are put together and connected to one another, for example, by means of ultrasonic welding, hot caulking or adhesive bonding. When doing so, the lens and the diaphragm aperture must be spatially positioned exactly in relation to one another in a way corresponding to the path of rays of the light. The joining together of the parts is only possible with great effort due to their tolerances and small size. Furthermore, having many individual parts necessitates a strict overall tolerance of the optical module.

SUMMARY OF THE INVENTION

The present invention addresses the disadvantages of the prior art by providing an analysis system whose effort and costs of assembling are reduced.

In one embodiment, the present invention provides an analysis system for analyzing a sample on an analytical test element, comprising a measuring module for carrying out measurements on the sample deposited on the analytical test element and an optical module. The optical module comprises a lens and a diaphragm by which the light can be focused. The lens and the diaphragm of the optical module are combined as one piece in a multi-component injection-molded part. The analysis system contains, inter alia, a measuring module for carrying out measurements on a sample on an analytical test element.

The sample is, for example, a body fluid, in particular, blood or interstitial fluid. The examination of blood samples or of interstitial fluid makes it possible in clinical diagnostics to provide early and reliable detection of pathological conditions and to carry out targeted and substantiated monitoring of physical states. Medical diagnostics relies on obtaining a sample of blood or interstitial fluid from the individual to be examined.

To obtain the sample, the skin may be punctured, for example, at the finger tip or the ear lobe of the person to be examined, with the aid of a sterile, sharp lancet. In this way a small amount of blood or interstitial fluid is obtained for the analysis. In particular, this method is suitable for the analysis of a sample that is carried out directly after the sample is obtained.

In particular in the area of so-called "home monitoring," in other words, where medically untrained people carry out simple analyses of their own blood or interstitial fluid, and where in particular diabetics need to obtain blood regularly several times a day to monitor blood glucose concentration, lancets and associated equipment (known as lancing devices) are offered, making it possible to reproducibly obtain samples with little pain.

To carry out the measurements, the sample is applied to an analytical test element, which contains reagents (for example, in a test area). When the reagents contact the sample, a reaction of the analyte contained in the sample with the reagents leads to a physically measurable change in the test element, which correlates with the concentration of the analyte.

The measuring module of the analysis system according to the invention measures this change. The measured values obtained in the measurements of the measuring module serve for determining the concentration of the analyte in the sample.

In the case of photometric analysis systems, the test elements contain a reagent system, the reaction of which with the analyte leads to a photometrically detectable change (a change in color). The reagents are in this case usually located in a test area of the test element, the color of which changes as a function of analyte concentration. This change in color can be determined quantitatively by reflection photometry with the aid of a measuring module.

Electrochemical test elements contain an electrochemical reagent system, the reaction of which with the analyte influences the voltage or potential between two poles of the test element and/or of the current intensity flowing between two poles of a test element with a defined voltage. In this case, the voltage or current intensity is therefore the physically measurable variable that is determined by a corresponding measuring module, which is integrated in the analysis system and is designed as a voltage or current measuring device. A change of current or voltage correlates with the concentration of the analyte and is converted into the analysis data (concentration of the analyte).

An optical module is generally a subassembly which contains, inter alia, at least a lens and a diaphragm. Light can be focused by the lens and the diaphragm. In this context, a lens generally refers to an optical component known to a person skilled in the art as an optical lens. In this context, a diaphragm refers to an optical component which comprises an opaque diaphragm body and a light-transmitting diaphragm aperture. The diaphragm prevents light from spreading in certain spatial directions. It serves for delimiting the cross section of beams and for reducing stray light.

In the analysis system according to these teachings, the lens and the diaphragm of the optical module are formed or combined as one piece in a multi-component injection-molded part. Injection molding is a process known in the art in which a plasticized material (injection molding compound), in particular, a thermoplastic or thermoset, is injected into a forming tool, i.e., an "injection mold," at high pressure and transformed there under pressure into the solid state. The injection-molded part can then be removed from the injection mold. Multi-component injection molding is likewise a process known in the art. In particular, so-called sandwich molding is suitable for producing the multi-component injection-molded part for the analysis device according to these teachings. In this case, two or more materials are injected one after the other into an injection mold, whereby they are joined together with a material bond at their interfaces. The geometry of the cavity present in the injection mold is changed between the two injections.

In the prior art, for example, a number of lenses are produced as a one-piece multi-component injection-molded part, as described for example in DE 102 61 974, US 2004/0120053 or DE 44 31 744.

In the case of the analysis system according to these teachings, the one-piece combination of the lens and the diaphragm of the optical module in the multi-component injection-molded part provides many advantages. It is no longer necessary for the lens and the diaphragm to be joined together after their production, thus dispensing with a working step in the production of the analysis system. As a consequence, costs are saved. The handling of the multi-component injection-molded part is easier than that of the individual lens and the individual diaphragm. A reproducibly exact unit of lens and diaphragm can also be mass-produced. There are no tolerances between the lens and the diaphragm. Therefore, exact positioning of the diaphragm in relation to the lens is ensured.

In the case of the analysis system according to exemplary embodiments, not only the lens and the diaphragm but also further lenses and/or further diaphragms and/or further component parts of the optical module may be combined in the injection-molded part of the optical module. If appropriate, the entire optical module can be a multi-component injection-molded part.

According to one embodiment of the present invention, two diaphragms and one or two lenses are combined in the multi-component injection-molded part. The multi-component injection-molded part is preferably a two-component injection-molded part, in particular, a two-component injection-molded part with a first, translucent plastic component and a second, opaque plastic component. The translucent plastic component is translucent with preference for light in a wavelength range from 200 to 1700 nm, with particular preference in a wavelength range from 600 to 950 nm, the opaque plastic component preferably being largely non-transmitting for light in this wavelength range. The lens integrated in the multi-component injection-molded part preferably consists of the translucent plastic. For this purpose, a region of the multi-component injection-molded part is formed from the translucent plastic in such a way that it assumes the function of an optical lens. An opaque plastic may be used, for example, for regions of the multi-component injection-molded part that assume the function of a diaphragm body. The translucent plastic component may, for example, contain at least one plastic selected from the group comprising acrylonitrile-butadiene-styrene polymers (ABS), methyl methacrylate-butadiene-styrene copolymers (MABS), polycarbonate (PC), polycarbonate blends (PCB), polysulfone (PSU) and polyether sulfone (PES). The opaque plastic component preferably contains at least one plastic selected from the group comprising acrylonitrile-butadiene-styrene polymers (ABS), polycarbonate blends (PCB) and polyether sulfone (PES).

According to an exemplary embodiment, the diaphragm comprises a diaphragm body of an opaque plastic and a diaphragm aperture, the diaphragm aperture being filled with the translucent plastic. The diaphragm aperture is therefore closed by a protective window of the translucent plastic, which prevents contaminants from passing through the diaphragm aperture. The lens and the diaphragm aperture can be filled with the translucent plastic to be combined in a contiguous region. They are in this case made of the translucent plastic and are combined in the multi-component injection-molded part. This simplifies the injection-molding process and the optical module and ensures fixed and defined positioning of the diaphragm aperture (or of the window) in relation to the lens.

The diaphragm in the optical module of the analysis system may, however, also comprise a diaphragm body of an opaque plastic and a diaphragm aperture, the diaphragm aperture being a clearance in the diaphragm body. The clearance is in this case not filled with material. As a result, less light is absorbed as it passes through the diaphragm aperture than if the diaphragm aperture is filled with a material.

According to an embodiment of the invention, the measuring module contains the optical module, the optical module serving for carrying out optical measurements on the sample on the analytical test element. In this case, in particular the measuring module, is typically intended for photometric measurements on the sample (for example, a human or animal body fluid) and is designed for determining the concentration of an analyte (for example, glucose) in the sample.

Currently known in the art, for example, is the ACCU CHEK® Compact analysis system from Roche Diagnostics, Germany. This system includes a measuring module which contains an optical module, the optical module being made up of two plastic parts, one of which contains a diaphragm with a plastic window as the diaphragm aperture and the other of which contains a lens. The parts are small (14.5×7.5×21 mm and 0.7×4×60 mm, respectively). The function of the measuring module in this analysis system is to position a test element for carrying out measurements and, with the aid of the optical module, to direct rays of light to determine blood sugar values optically. The two plastic parts of the optical module in this analysis system are connected to one another by ultrasonic welding. High costs are incurred by joining together the two parts. Further, the small overall size of the parts makes handling very complicated. The welding requires an additional operation, which is carried out with great effort. Additional tolerances are imposed as a result of using two parts and cannot be avoided. The position of the diaphragm is also determined here by its production tolerances.

In the analysis system according to these teachings, the measuring module contains an optical module in which at least one lens and at least one diaphragm are combined as one piece in a multi-component injection-molded part. The entire optical module contained in the measuring module can be a two-component injection-molded part, in which at least one lens and at least one diaphragm are contained. An advantage of this configuration is that the complete optical module can be injection-molded in one operation. For this purpose, the optical path of rays may have to be recalculated and the optical components contained in the optical module may have to be differently designed.

The measuring module in the analysis system according to these teachings typically comprises a light source, a detector and a test element holder, which are arranged in such a way that light from the light source can pass through a translucent region of the multi-component injection-molded part to a test element arranged in the test element holder and be reflected by the test element through the translucent region to the detector. The light source is, for example, a light-emitting diode (LED). The detector is, for example, a photodiode. The test element holder receives a test element, in particular, during the carrying out of the measurements with the optical module. It is designed for guiding during the manual or automatic placement of the test element into the measuring module and for the exact positioning of the test element during the measurements. During the measurements, the test element is positioned in the test element holder in such a way that the light from the light source is directed via the translucent region of the multi-component injection molded part onto a test area on the test element containing the sample and reagents. Depending on the concentration of the analyte in the sample, a portion of the light hitting the test element is reflected at it in such a way that it passes through the translucent region of the multi-component injection-molded part to the detector.

According to another embodiment, the measuring module comprises a light source, a detector and a test element holder, which are arranged in such a way that light from a light source can pass through a translucent region of the multi-component injection-molded part to a test element arranged in the test element holder and be transmitted to the detector.

According to a further embodiment, the analysis system contains a reading module for reading optically coded data, the reading module containing the optical module or a further optical module.

Analysis systems that contain a storage container (magazine) with a multiplicity of test elements are known in the art. In these systems, a test element is transported, for example, by a slide or pushrod from the magazine to the site of the measurement in the measuring module and, after carrying out the measurement, is automatically ejected from the analysis system or re-magazined in the magazine. For example, DE 199 02 601 A1 discloses a device for removing an analytical consumable, in particular a test element, from a storage container that has one or more chambers which contain the consumables. The chambers respectively have a removal opening for removing a consumable and a push-in opening, opposite the removal opening, for inserting a pushrod for transporting the consumable. The removal opening and the push-in opening are closed with a film to store the consumable. The device comprises a pushrod, which can be made to move by means of a drive unit for the removal of a consumable.

In the ACCU CHEK® Compact analysis system from Roche Diagnostics, Germany, there is contained, for example, a reading module (with a barcode reader), which can read a barcode on the outer surface of a test element magazine in the form of a drum that is placed into the analysis system. The barcode contains, for example, information on the test elements contained in the magazine that are relevant for the evaluation of the data measured by the measuring module and are taken into consideration in the evaluation. The reading module contains two individual plastic injection-molded parts and a printed circuit board, which are joined together during the production of the reading module. The one injection-molded part contains a diaphragm and the other contains a lens arrangement. The printed circuit board and the two injection-molded parts are connected to one another in a complicated adhesive-bonding operation. The joining together is only possible in this case with great effort. One reason for this is the tight tolerances required for the injection-molded parts. Handling is also problematic because of the small size of the parts. The many individual parts result in tight overall tolerances for the optical module.

In one embodiment of the present invention, the two injection-molded parts are combined as one piece in a multi-component injection-molded part. Consequently, the position of the diaphragm and the lens relative to one another can be controlled exactly and the disadvantages mentioned can be avoided.

No adhesive-bonding operation is necessary between the diaphragm and the optical module. Reproducibly exact parts are also obtained in mass production. The handling of the three-component injection-molded part is easier than the handling of the two individual parts. There are no tolerances between the optical module and the diaphragm. The construction is less expensive, so that a cost savings is achieved.

The printed circuit board of the reading module can be subsequently attached to the multi-component injection-molded part. The printed circuit board carries, for example, a detector (for example a photodiode) and a light source (for example an LED).

According to one embodiment, the reading module comprises a light source, a detector and a magazine holder, which are arranged in such a way that light from the light source can pass through a translucent region of the multi-component injection-molded part to a test element magazine held in the magazine holder and be reflected by the test element magazine through the translucent region to the detector.

The printed circuit board, which carries the detector and the light source, is preferably positioned, with the aid of pins engaging in recesses, in relation to the multi-component injection-molded part and then connected to the latter, for example by adhesive bonding, ultrasonic welding or hot caulking. In this case, the multi-component injection-molded part has recesses and/or pins and the printed circuit board has matching pins and/or recesses.

These teachings also relate to a method for producing an analysis system for analyzing a sample on an analytical test element, the analysis system containing a measuring module and an optical module, the optical module comprising a lens and a diaphragm, characterized by (a) multi-component injection molding of a one-piece multi-component injection-molded part, in which the lens and the diaphragm are combined, and (b) positioning and mounting of the multi-component injection-molded part in the analysis system.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
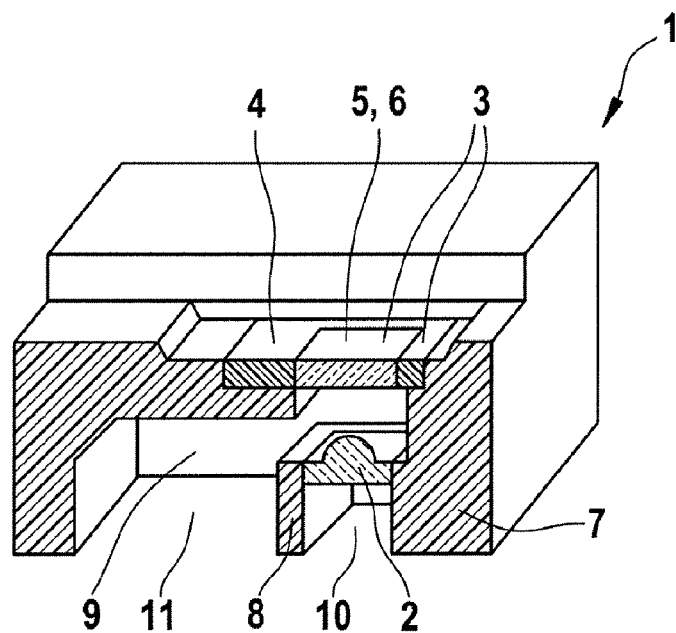
FIG. 1 is a sectional perspective view illustrating an optical module which is contained in a measuring module of an analysis system from the prior art.

FIG. 1 shows a section through an optical module which is contained in a measuring module of an analysis system from the prior art. The optical module 1 comprises a lens 2 and a diaphragm 3, which contains a diaphragm body 4 and a diaphragm aperture 5. The diaphragm aperture 5 is filled by a translucent window 6. The lens 2 and the diaphragm 3 are individual components, which are adhesively bonded to an optical module base body 7. The mount 8 of the lens 2 serves as a further diaphragm. In the optical module base body 7 there is a large cavity 9 and a small cavity 10. Rays of light from a light source (not represented) can pass from the small cavity 10 through the lens 2, through the large cavity 9 and through the translucent window 6, to a test element (not represented), which is located above the diaphragm 3 in a test element holder. Light reflected by the test element can then pass back through the window 6 into the large cavity 9 and from there through an opening 11 to a detector (not represented). This optical module has many individual parts that are adhesively bonded to one another and has the disadvantages of the prior art mentioned above.

Figure 2:
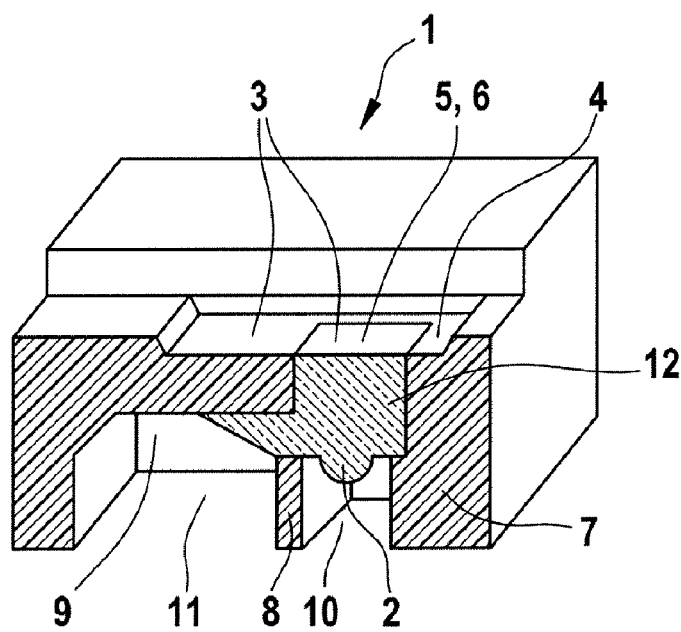
FIG. 2 is a sectional perspective view of an optical module which is contained in a measuring module of an analysis system according to an embodiment of the present invention.

FIG. 2 shows a section through an optical module, which is contained in a measuring module of an analysis system according to an embodiment of the present invention. The optical module 1 is in this case a two-component injection-molded part, which combines the diaphragm 3 (including the diaphragm body 4 and the window 6 serving as the diaphragm aperture 5), the lens 2 and the optical module base body 7 as one piece. The optical module base body 7, the diaphragm body 4 and the mount 8 of the lens 2 are in this case injection-molded from an opaque plastic. The lens 2 and the window 6 in the diaphragm aperture 5 are combined in a continuous region 12 of a translucent plastic in the two-component injection-molded part.

Figure 3:
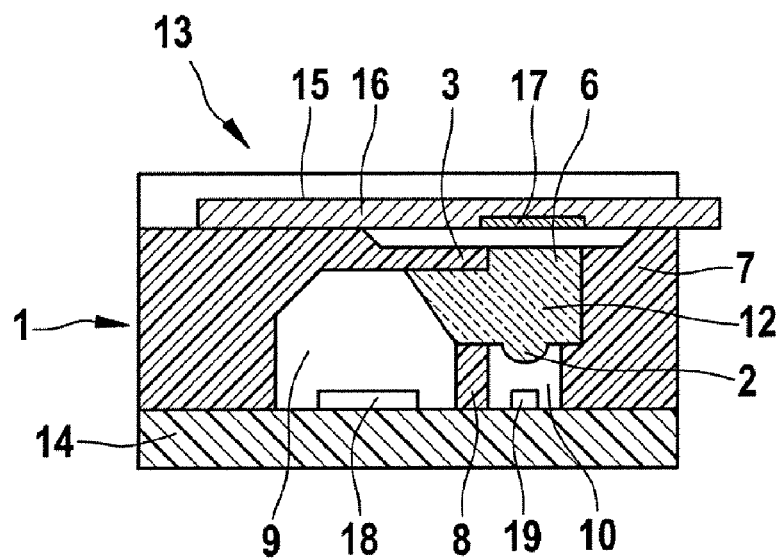
FIG. 3 is a sectional view of a measuring module of an analysis system with a test element.

FIG. 3 shows a section through a measuring module of an analysis system with a test element. Contained in the measuring module 13 are an optical module 1 according to FIG. 2 and a printed circuit board 14. The optical module 1 comprises the optical module base body 7, the lens 2, the diaphragm 3, the mount 8 of the lens 2, the cavities 9, 10 and a test element holder 15. The optical module 1 is configured as a two-component injection-molded part with a first, translucent plastic component (region 12) and a second, opaque plastic component. In the test element holder 15 there is a strip-shaped analytical test element 16 having a test area 17 in which a sample to be analyzed is located, is arranged above the window 6.

On the printed circuit board 14 there are a detector 18 and a light source 19, which protrude into the large cavity 9 and into the small cavity 10, respectively. The printed circuit board 14 can be, for example, adhesively fixed to the two-component injection-molded part.

Figure 4:
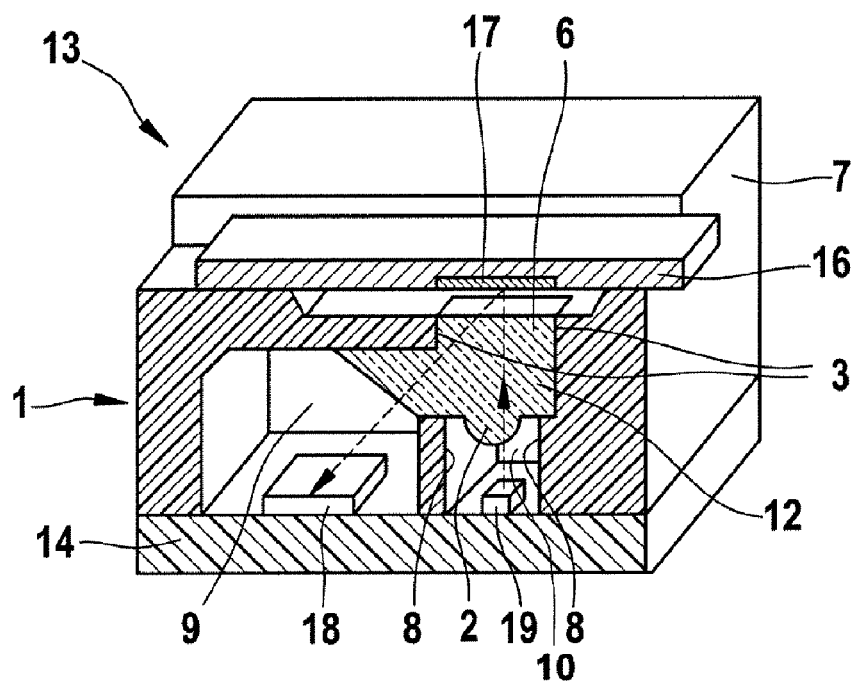
FIG. 4 is a sectional perspective view illustrating the path of rays in the measuring module according to FIG. 3.

FIG. 4 shows the path of rays in the measuring module according to FIG. 3. A light source 19 emits light for the photometric analysis of a sample on the test area 17 of the test element 16, which is focused onto the test element 16 by the continuous translucent region 12. The optical properties (for example, coloration) on the test area 17 are determined. Specifically, part of the light is reflected from the test element 16 and returns through the region 12 into the large cavity 9 to the detector 18, from the signal of which the concentration of an analyte in the sample can be determined. For example, an evaluation module (not shown) of the analysis system according to the invention can be employed for determining analyte concentration.

Figure 5A:
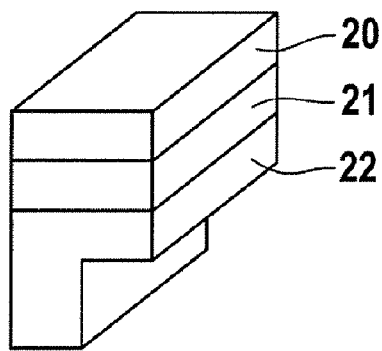
FIGS. 5a and 5b are perspective views that schematically show a comparison of component parts of a reading module in an analysis system from the prior art and in an analysis system according to the invention, respectively.

The prior art reading module shown in FIG. 5a includes a printed circuit board 20, a diaphragm 21 and a lens arrangement 22 with at least one lens, these being produced as three separate components and subsequently joined together.

Figure 5B:
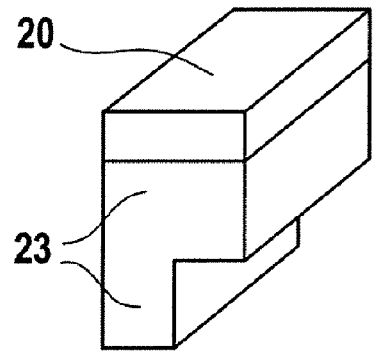

According to an exemplary embodiment of the present invention shown in FIG. 5b, in the reading module, the lens arrangement and the diaphragm are combined as a one-piece multi-component injection-molded part 23. The multi-component injection-molded part is joined together with the printed circuit board 20.

Figure 6:
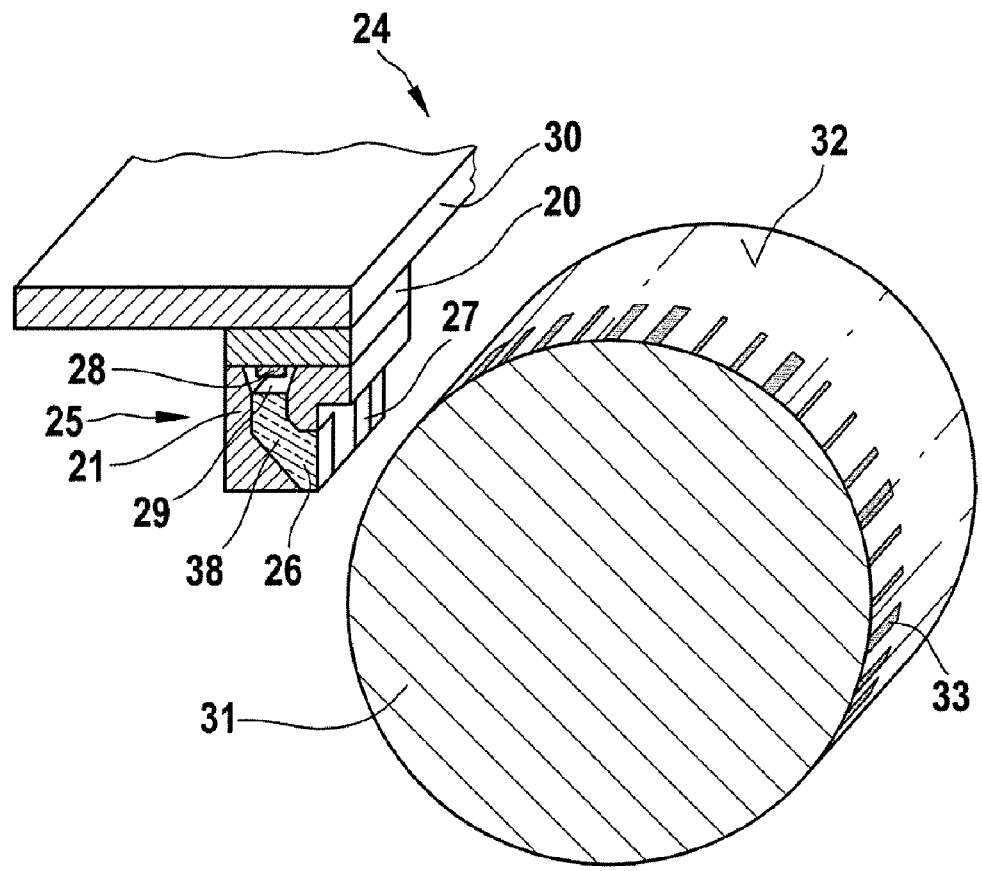
FIG. 6 is a perspective view that schematically shows a reading module in an analysis system according to the invention.

FIG. 6 schematically shows a reading module in an analysis system according to an embodiment of the invention. The reading module 24 contains, inter alia, an optical module 25 and a printed circuit board 20. In the optical module 25, a first lens 26 (shown in section), a second lens 27 and a diaphragm 21 are combined to form a one-piece two-component injection-molded part. The lenses 26, 27 are injection-molded from a first, translucent component (translucent region 38) and the diaphragm 21 is injection-molded from a second, opaque component. The printed circuit board 20 is connected to the optical module, for example, by means of an adhesive bond. It carries a light source 28 and a detector (not shown), which protrude into cavities 29 of the optical module 25. The printed circuit board is, for example, attached to an analysis system board 30.

Also represented in FIG. 6 is a test element magazine 31 in the form of a drum, which serves for storing a multiplicity of test elements. On its circumferential surface 32, the magazine 31 has a barcode 33, which the reading module 24 can read. The magazine 31 is located in a magazine holder in the reading module 24, whereby it is positioned in relation to the optical module 25 for reading the barcode 33.

Figure 7:
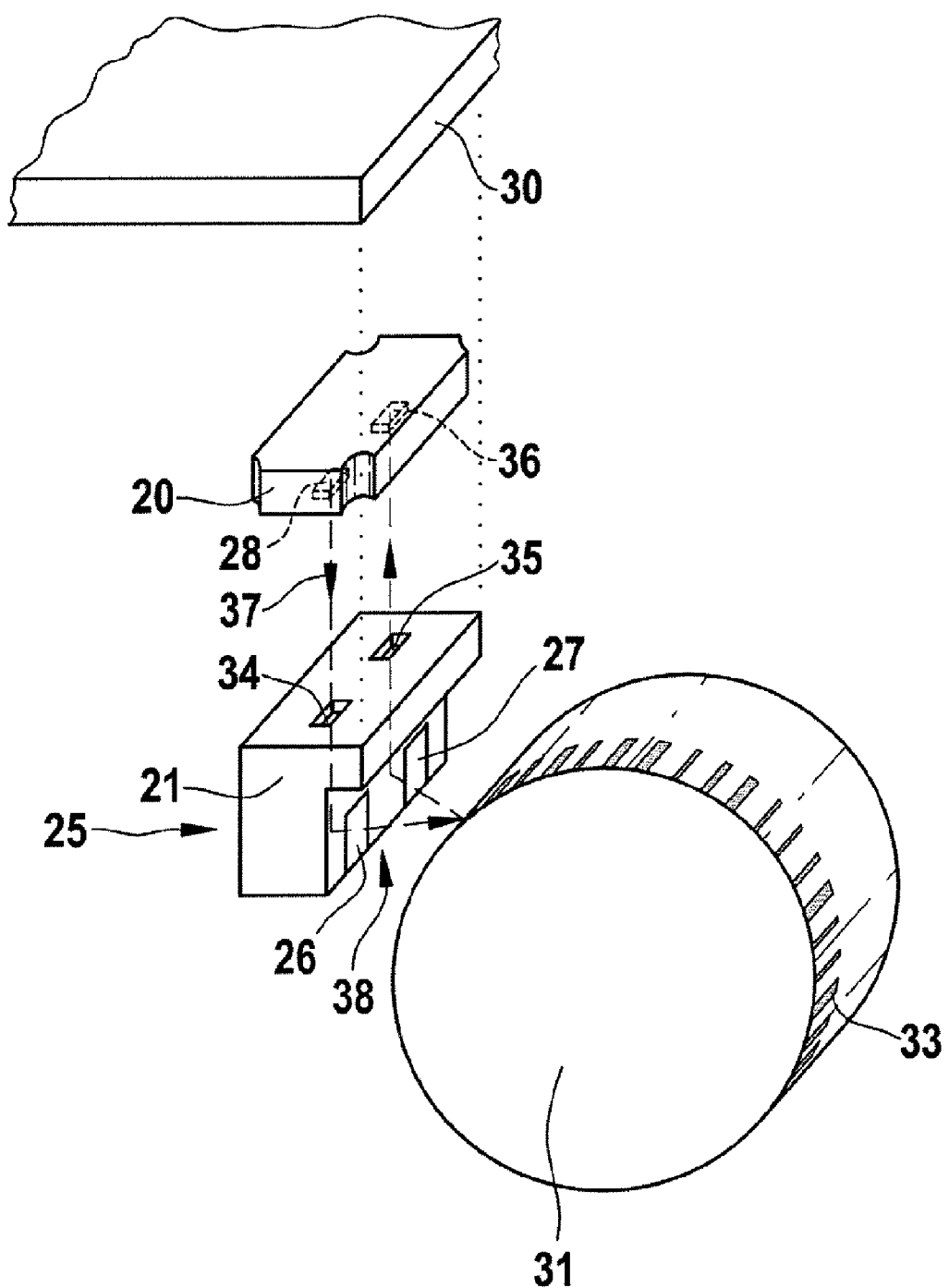
FIG. 7 is an exploded perspective view that shows the path of rays in the reading module from FIG. 6.

FIG. 7 shows the path of rays in the reading module from FIG. 6. For clarity, the analysis system board 30, the printed circuit board 20 and the optical module 25 are shown exploded away. The path of rays 37 is indicated by arrows. Light from a light source 28 propagates through the first cavity 34, the diaphragm 21 and the translucent region 38, including the first lens 26, to the barcode 33, is reflected by it and reaches the detector 36 through the translucent region 38 with the second lens 27, the diaphragm 21 and the second cavity 35.

Figure 8:
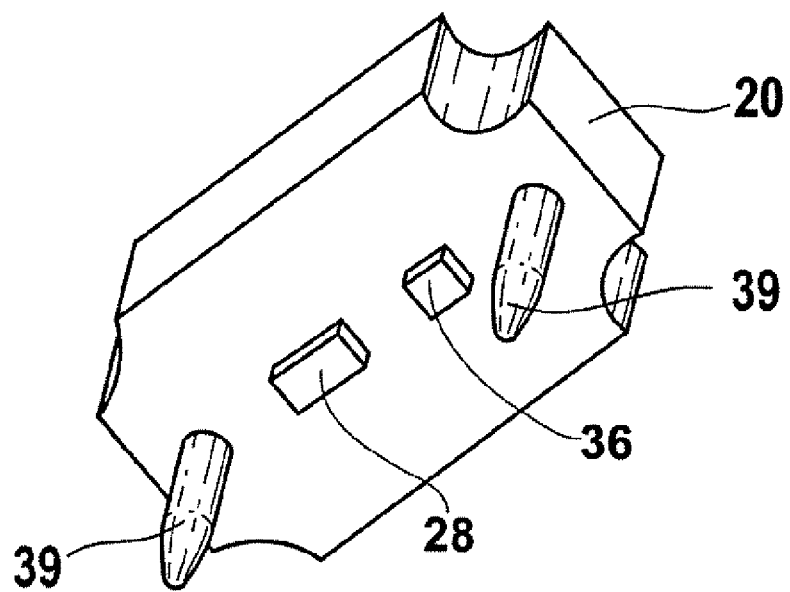
FIG. 8 is an exploded perspective view that shows the printed circuit board and multi-component injection-molded part of an analysis system according to the invention.
Figure 8:
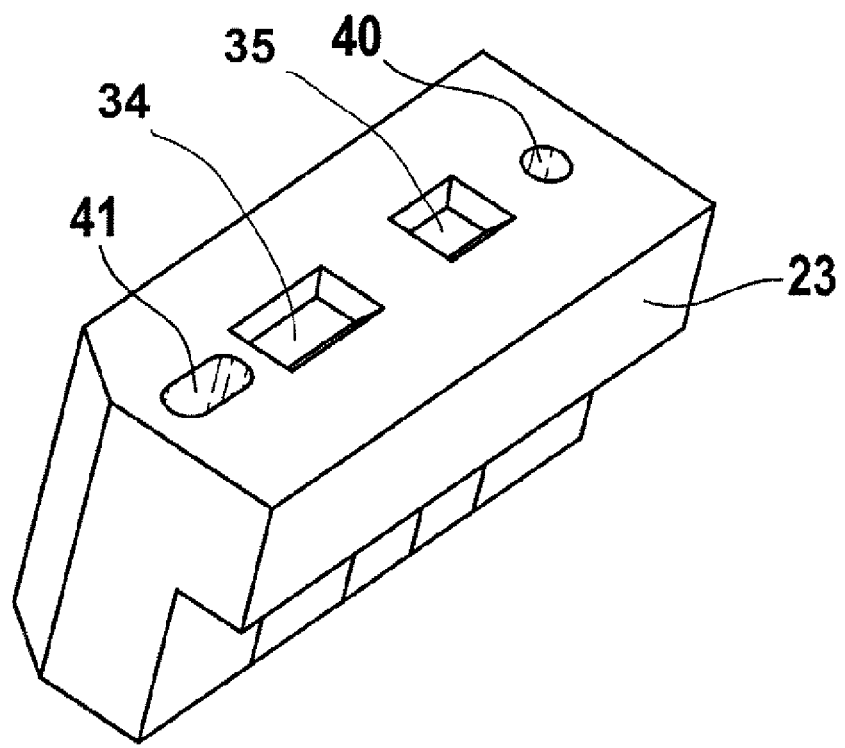

FIG. 8 demonstrates how the printed circuit board and the multi-component injection-molded part can be connected to one another in an analysis system according to exemplary embodiments. For this purpose, the printed circuit board 20 has two pins 39, which can engage in openings provided for them (bore 40 and oblong hole 41) in the multi-component injection-molded part 23. In this case, the light source 28 and the detector 36 are positioned in such a way that they are aligned exactly within the cavities 34, 35, respectively. Then, the two parts 20, 23 are joined together by a joining process known to a person skilled in the art. The multi-component injection-molded part 23 is, for example, the optical module of a reading module.

Figure 9A:
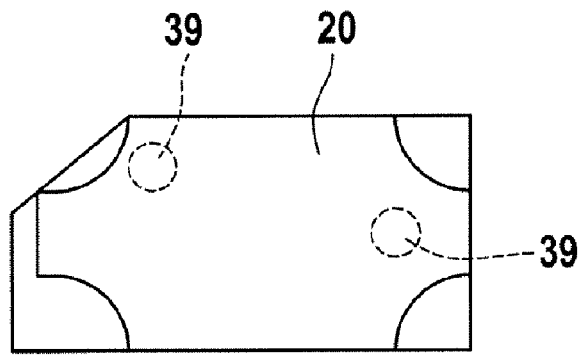
FIGS. 9a-9c are plan views that illustrate various ways of attaching the printed circuit board to the multi-component injection-molded part.
Figure 9B:
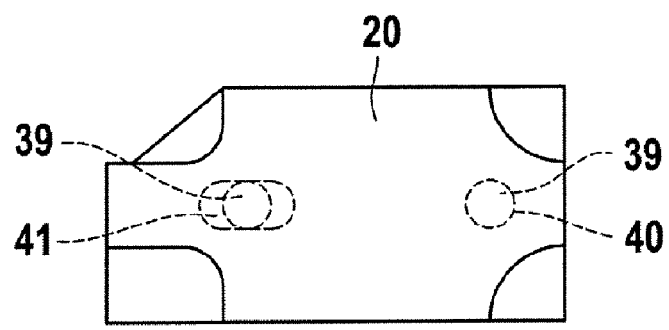
Figure 9C:
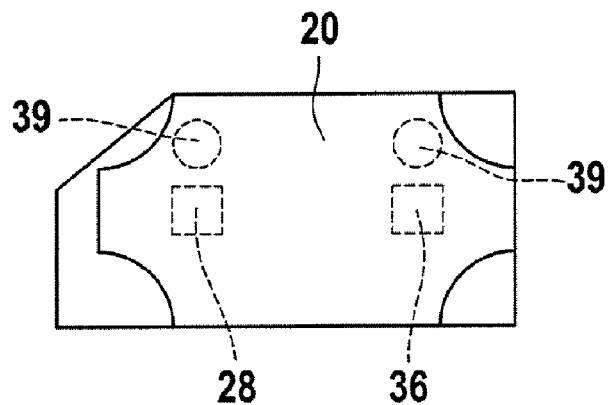

FIGS. 9a-9c show various ways of attaching the printed circuit board. In FIG. 9a, the printed circuit board 20 has two pins 39, which are offset relative to one another. FIG. 9b corresponds to the variant shown in FIG. 8, with two pins 39 that lie along a central line and engage a bore 40 and a milled oblong hole 41. In FIG. 9c, the two pins 39 lie on a common lateral line and spaced away from the light source 28 and of the detector 36, respectively.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS 1 optical module
2 lens
3 diaphragm
4 diaphragm body
5 diaphragm aperture
6 translucent window
7 optical module base body
8 mount of the lens
9 large cavity
10 small cavity
11 opening
12 continuous region
13 measuring module
14 printed circuit board
15 test element holder
16 test element
17 test area
18 detector
19 light source
20 printed circuit board
21 diaphragm
22 lens arrangement
23 multi-component injection-molded part
24 reading module
25 optical module
26 first lens
27 second lens
28 light source
29 cavities
30 analysis system board
31 test element magazine
32 circumferential surface
33 barcode
34 first cavity
35 second cavity
36 detector
37 path of rays
38 translucent region
39 pins
40 bore
41 oblong hole

What is claimed is:

1. An analysis system for analyzing a sample on an analytical test element, comprising:
   a measuring module for carrying out measurements on the analytical test element;
   an optical module having a lens and a diaphragm by which light can be focused; and
   the lens and the diaphragm of the optical module together comprising a one piece multi-component injection molded part; wherein, the diaphragm comprises a diaphragm body of an opaque plastic and a diaphragm aperture that is filled with a translucent plastic, the lens is formed from the translucent plastic, and the lens and the diaphragm aperture comprise a continuous region of the translucent plastic.

2. The analysis system of claim 1, wherein the measuring module contains the optical module, the optical module being adapted to carry out optical measurements on a sample deposited on the analytical test element.

3. The analysis system of claim 2, wherein the measuring module comprises a light source, a detector, a test element holder and a test element arranged in the test element holder, the measuring module being arranged such that light from the light source passes through a translucent region of the multi-component injection-molded part to the test element and is reflected by the test element through the translucent region to the detector.

4. The analysis system of claim 1, further comprising a reading module configured to read optically coded data, the reading module containing the optical module or a further optical module.

5. The analysis system of claim 4, wherein the reading module comprises a light source, a detector and a magazine holder arranged such that light from the light source passes through a translucent region of the multi-component injection-molded part to a test element magazine held in the magazine holder and is reflected by the test element magazine through the translucent region to the detector.

6. The analysis system of claim 5, wherein the light source and the detector are arranged on a printed circuit board which is connected to the optical module.

7. A method for producing an analysis system for analyzing a sample on an analytical test element, the analysis system containing a measuring module and an optical module, the optical module comprising a lens and a diaphragm, the method comprising the following steps:
   injection molding the lens and the diaphragm as a one-piece multi-component injection-molded part; forming the diaphragm with a diaphragm body of an opaque plastic and a diaphragm aperture that is filled with a translucent plastic;
   forming the lens from the translucent plastic, wherein the lens and the diaphragm aperture comprise a continuous region of the translucent plastic; and
   positioning and mounting the multi-component injection-molded part in the analysis system.

8. The method of claim 7, wherein the injection molding of the lens and the diaphragm comprises sandwich molding.

9. The method of claim 7, wherein the injection molding of the diaphragm and the lens are performed in separate steps.

10. A device for the photometric evaluation of test elements, comprising:
   a test element holder configured to hold a test element;
   a light source configured to illuminate a test element held in the test element holder;
   a lens and diaphragm positioned between the light source and the test element holder to focus light from the light source, the lens and diaphragm being formed as a one-piece injection molded part; and
   the diaphragm defining an aperture that is filled with translucent plastic, wherein the lens and diaphragm aperture define a continuous region of translucent plastic.

11. The device of claim 10, wherein the one piece injection molded part comprises an opaque plastic defining the diaphragm.

12. The device of claim 10, further comprising a detector, wherein during use of the device, light from the light source passes through the continuous region of the translucent plastic to a test element held in the test element holder and is reflected by the test element through the continuous region of the translucent plastic to the detector.

13. The device of claim 10, further comprising a reading module configured to read optically coded data, the reading module containing the optical module or a further optical module.

14. The device of claim 10, further comprising a detector and a printed circuit board, wherein the light source and the detector are arranged on the printed circuit board.

* * * * *